United States Patent [19]

Koeffer et al.

[11] Patent Number: 5,041,684

[45] Date of Patent: Aug. 20, 1991

[54] HYDROFORMYLATION

[75] Inventors: Dieter Koeffer, Weinheim; Werner Bertleff, Viernheim; Michael Roeper, Wachenheim, all of Fed. Rep. of Germany

[73] Assignee: BASF Aktiengesellschaft, Ludwigshafen, Fed. Rep. of Germany

[21] Appl. No.: 557,065

[22] Filed: Jul. 25, 1990

[30] Foreign Application Priority Data

Jul. 26, 1989 [DE] Fed. Rep. of Germany ....... 3924720

[51] Int. Cl.$^5$ .............................................. C07C 45/50
[52] U.S. Cl. ..................................... 568/454; 568/451
[58] Field of Search ................................ 568/454, 451

[56] References Cited

U.S. PATENT DOCUMENTS

| | | |
|---|---|---|
| 988,941 | 4/1911 | Keefe . |
| 988,943 | 4/1911 | Lentz . |
| 1,197,847 | 9/1916 | Osborn . |
| 3,527,809 | 9/1979 | Pruett et al. ........................ 260/604 |
| 3,917,661 | 11/1975 | Pruett et al. ................. 260/410.9 R |
| 4,258,215 | 3/1981 | Dawes ................................. 568/454 |
| 4,533,757 | 8/1985 | Kummer et al. ..................... 568/454 |
| 4,711,968 | 12/1987 | Oswald et al. ....................... 568/454 |
| 4,778,905 | 10/1988 | Besson et al. ........................ 568/454 |
| 4,778,929 | 10/1988 | Zehner et al. ....................... 568/454 |
| 4,889,957 | 12/1989 | Besson et al. ....................... 568/454 |

FOREIGN PATENT DOCUMENTS

| | | |
|---|---|---|
| 0114611 | 8/1984 | European Pat. Off. . |
| 0179004 | 4/1986 | European Pat. Off. . |
| 0179004 | 4/1986 | European Pat. Off. ............ 568/454 |
| 0254180 | 1/1988 | European Pat. Off. . |
| 1186455 | 4/1965 | Fed. Rep. of Germany ...... 568/454 |
| 1793069 | 11/1979 | Fed. Rep. of Germany . |
| 3301591 | 7/1984 | Fed. Rep. of Germany ...... 568/454 |

OTHER PUBLICATIONS

New Syntheses with Carbon Monoxide, (1980) pp. 73–77.
J. Chem. Soc., Chem. Commun., 1983, 510–511.
Journal of Organometallic Chem. 302 (1986)C17–C20.
Chem. Eng. Dee, p. 110 (1977).

*Primary Examiner*—Werren B. Lone
*Attorney, Agent, or Firm*—Keil & Weinkauf

[57] ABSTRACT

Olefinically unsaturated compounds are hydroformylated in an organic reaction medium with the aid of rhodium complex catalysts which are soluble in the reaction medium by performing the reaction in the presence of water-insoluble rhodium complex catalysts and also in the presence of arylthiols of the general formula I Ar—SH    I where Ar is substituted or unsubstituted aryl.

5 Claims, No Drawings

HYDROFORMYLATION

The present invention relates to a process for hydroformylating olefinically unsaturated compounds in an organic reaction medium with the aid of rhodium complex catalysts which are soluble in the reaction medium.

The hydroformylation of olefinically unsaturated compounds by means of rhodium complex catalysts dissolved homogeneously in the organic reaction medium is common knowledge, for example from Chem. Eng. Dec. 1977, 110 ff, or from DE-A-3 301 591, DE-A-1 793 069 and DE-A-1 186 455. The catalyst is stabilized and the selectivity for n-aldehydes is improved by adding phosphine or phosphite ligands to the reaction medium, in a high molar excess based on the rhodium used as catalyst.

Used in an industrial hydroformylation process, the rhodium catalyst gradually loses activity. The cause of this deactivation is thought to reside on the one hand in catalyst poisons which are introduced into the reaction medium with the starting materials and on the other in degradation reactions of the phosphorus ligands. Known catalyst poisons are in particular sulfur compounds such as hydrogen sulfide and carbonyl sulfide, which is why these compounds must be removed as completely as possible from the feedstock streams of the hydroformylation process (cf. B. Cornils, in J. Falbe, New Syntheses with Carbon Monoxide, in particular p. 73-77, Springer, Berlin 1980).

Of the degradation reactions of the phosphorus ligands it is known that, for example, triphenylphosphine in the hydroformylation of propene is first converted into alkyldiphenylphosphines and dialkylphenylphosphines such as propyldiphenylphosphine, butyldiphenylphosphine and dipropylphenylphosphine, which are then further degraded (cf. B. Cornils in J. Falbe, New Syntheses with Carbon Monoxide, (1980), p. 73-77).

It is true that, according to US-A-4 711 968, it is also possible to hydroformylate sulfur-containing cracker distillates with the aid of cobalt or rhodium complex catalysts, but the sulfur compounds contained in these distillates are predominantly thiophenes and benzothiophenes which do not have an inhibitory effect on the hydroformylation catalysts and only to a minor extent thiols, whose adverse effect on these catalysts has been sought to be suppressed by a whole series of measures, for example the employment of a higher carbon monoxide partial pressure.

Kalck et al. describe the hydroformylation with t-butylthiolate-bridged bicyclic rhodium complexes having phosphite ligands (J. Chem. Soc. Chem. Com. 1983, 510-511) or phosphine ligands (J. Organometal. Chem. 302 (1986), C17-C20). Bicyclic water-soluble rhodium complexes bridged with t-butylthiolate as thiol species and containing triarylphosphinetrisulfonate ligands are also preferred in EP-A-l79 004, although said reference also describes the preparation of arylthiolate-bridged water-soluble rhodium triarylphosphinetrisulfonate complexes. These t-butylthiolate-bridged rhodium complex catalysts show higher reactivity and better selectivity than conventional rhodium complex catalysts in laboratory tests. When used in continuous hydroformylation pilot plants, however, these t-butylthiolate-bridged rhodium complexes are found to remain largely ineffective and it is also observed that t-butylthiol gradually disappears from the reaction medium together with the hydroformylation products.

It is an object of the present invention to provide a process for hydroformylating olefinically unsaturated compounds with the aid of water-insoluble rhodium catalysts which prevents the deactivation of the rhodium catalyst as a consequence of degradation reactions of the phosphine or phosphite ligands and improves the long-term selectivity and stability of the catalyst.

We have found that this object is achieved by a process for hydroformylating olefinically unsaturated compounds in an organic reaction medium with the aid of a rhodium complex catalyst which is soluble in the reaction medium, which comprises performing the reaction in the presence of a water-insoluble rhodium complex catalyst and also in the presence of an arylthiol of the general formula I $$Ar-SH \qquad \qquad I$$

where Ar is substituted or unsubstituted aryl.

Suitable arylthiols I for the process according to the present invention are unsubstituted arylthiols such as thiophenol, 1-naphthalenethiol, 2-naphthalene-thiol, 1-anthracenethiol and 1-phenanthrenethiol and $C_1$-$C_4$-alkyl- and/or -alkoxy-monosubstituted, -disubstituted or -trisubstituted thiols such as 2-methylthiophenol, 3-methylthiophenol, 4-methylthiophenol, 2,4-dimethylthiophenol, 3,4,5-trimethylthiophenol, 4-ethylthiophenol, 4-n-propylthiophenol, 4-isopropylthiophenol, 4-t-butylthiophenol, 4-methoxythiophenol and 4-t-butoxythiophenol. These compounds are commercially available or are simple to synthesize, for example as described in Houben-Weyl, Methoden der Organischen Chemie, Volume IX, ages 7-42, Thieme, Stuttgart 1955. In general, unsubstituted arylthiols are used. It will be readily understood that instead of these arylthiols it is also possible to add compounds to the reaction mixture which, under the conditions of the hydroformylation reaction, are convertible into the arylthiols I, for example the corresponding diaryl disulfides.

According to the present invention, the arylthiols I are added to the reaction mixture in a molar ratio of from 0.1 to 20 mol/mol of rhodium, preferably in a molar ratio of from 1 to 5 mol/mol of rhodium.

The hydroformylation catalysts used are in general water-insoluble rhodium complexes containing triorganophosphorus compounds as ligands, as described for example in US-A-4 277 627 and US-A-3 527 809 and also US-A-3 917 661. Preference is given to using triarylphosphines or alkyldiarylphosphines and also trialkyl, triaryl, dialkylaryl or alkyldiaryl phosphites. Particularly preferred triorganophosphines are triarylphosphines such as triphenylphosphine and tritolylphosphine and alkylarylphosphines such as n-hexyldiphenylphosphine; of the triorganophosphites, preference is given to using triphenyl and tritolyl phosphite.

The triorganophosphorus compounds are used in the process according to the present invention in a molar ratio of from 1 to 500, preferably from 1 to 150, mol/mol of rhodium.

Advantageously, the rhodium complex catalysts are generated in the hydroformylation mixture in situ from rhodium salts, for example from rhodium acetate or rhodium acetonylacetonate, and the desired triorganophosphorus ligands. It is of course also possible to use separately prepared rhodium complexes such as hydridocarbonyltris(triphenylphosphine)rhodium. The same is true of the addition of the arylthiols I according to the present invention. They are advantageously added to the hydroformylation mixture in the same way as the rhodium and the triorganophosphorus components of the catalyst.

The hydroformylation of olefins using the arylthiol-modified rhodium catalysts according to the present invention is carried out at a pressure of advantageously 1-300, preferably 1-50, bar and at a temperature of in general 50°-160° C. The other conditions of the process, for example the use of solvents, the use of a circulating gas, the recycling of the catalyst and the carbon monoxide/hydrogen concentration ratios, are state of the art and may be taken for example from the previously cited references U.S. Pat. Nos. 4,277,627, 3,527,809, 3,917,661, 4,533,757, GB-B-988 941 and GB-B-988 943.

The process according to the present invention can be used to hydroformylate not only α-olefins, such as ethene, propene, 1-butene, 1-hexene, 1-octene or 1-decene, but also olefins having an internal double bond, such as 2-butene, 2-hexene or 3-hexene, and also olefins substituted by substituents which are inert under the reaction conditions, for example allyl alcohol, allyl acetate, acrylic esters, acrylonitrile or acrolein acetals.

The process according to the invention makes it possible to achieve effective suppression of the degradation of the phosphorus ligands and hence of the gradual deactivation of the catalyst. This significantly reduces the loss of phosphorus ligands due to undesirable degradation reactions and reduces the catalyst costs of the process. Furthermore, the process according to the present invention makes it possible to achieve high selectivities for n-aldehydes without requiring a high molar excess of phosphine or phosphite ligands relative to rhodium.

EXAMPLE 1

In an experimental reactor, 236 g of propene per hour are hydroformylated at 105° C. and 20 bar in the presence of 120 ppm of rhodium, 0.37% by weight of triphenylphosphine (P/Rh:120 mol/mol), 128 ppm thiophenol (S/Rh:1.0 mol/mol) - the quantities are based on the amount of reaction mixture - and 1000 g of Texanol ® (=isomer mixture of 2,2,4-trimethylpentane-1,3-diol 3-monoisobutyrate) as solvent. The reactor was charged with carbon monoxide/hydrogen gas mixture, hydrogen and circulating gas at such rates that a constant circulating gas rate of 480 standard l/h and an off-gas rate of 30 standard l/h produced a carbon monoxide content of the circulating gas from 4 to 5% by volume and a hydrogen content of the circulating gas of about 70% by volume. The liquid discharge from the reactor was depressurized and separated in a thin-film evaporator into a butyraldehyde distillate and a catalyst-containing bottom product. The catalyst-containing product was continuously recycled into the reactor.

The yield of butyraldehyde decreased from 62.2% to 58.4% in the course of 21 days. The n-content was 84%.

At the end of the run the reaction mixture had a sulfur content corresponding to an S/Rh molar ratio of 1.1 mol/mol.

Table 1 shows the rate of ligand degradation compared with that of comparative Example A (hydroformylation in the absence of an arylthiol).

In the tables which follow, the abbreviations have the following meanings: Ph is phenyl, Pr is propyl and Bu is butyl.

COMPARATIVE EXAMPLE A

The experiment was carried out in the same way as in Example 1, except that no thiophenol was added.

The yield of butyraldehyde decreased from 76.8% to 60.9% over 21 days. The n-content was 80%. Table 1 shows the rate of ligand degradation.

EXAMPLE 2 AND COMPARATIVE EXAMPLES B AND C

Carried out in the same way as Example 1, except that 236 g of propene per hour were hydroformylated at 120° C. in the presence of 120 ppm of rhodium, 0.37% by weight of triphenylphosphine and a thiol as indicated in Table 2.

The rates of formation of phosphine degradation products in course of a run of 108 h are compared in Table 2.

EXAMPLES 3 TO 6 AND COMPARATIVE EXAMPLES D AND E

A mixture of 60 g of 1-octene, 60 g of toluene and 29.6 mg (0.12 mmol) of (acetylacetonato)dicarbonylrhodium and also phosphine and an arylthiol as indicated in Table 3 was hydroformylated in a 300-ml autoclave at 100° C. and 30 bar with a carbon monoxide/hydrogen gas mixture ($CO/H_2$:1 mol/mol) for 3 h. The liquid discharge from the reactor was analyzed by gas chromatography. The results are shown in Table 3.

TABLE 1

| Length of run | Example 1 | | | Comparative Ex. A | | |
|---|---|---|---|---|---|---|
| (h) | 180 | 348 | 516 | 180 | 348 | 516 |
| Phosphine degradation products in reaction solution (mmol/kg): | | | | | | |
| $PPh_2Pr$ | 1.91 | 3.87 | 6.25 | 5.43 | 14.9 | 21.0 |
| $PPh_2Bu$ | 0.04 | 0.10 | 0.17 | 0.26 | 1.94 | 3.37 |
| $PPhR_2$ (R = Pr, Bu) | 0.06 | 0.06 | 0.14 | 0.16 | 1.09 | 2.65 |
| Average rate of formation of phosphine degradation products (mmol/kg × d): | | | | | | |
| $PPh_2Pr$ | | 0.30 | | | 0.98 | |
| $PPh_2Bu$ | | 0.008 | | | 0.16 | |
| $PPhR_2$ (R = Pr, Bu) | | 0.007 | | | 0.12 | |

TABLE 2

| | Example 2 | Comparative Example B | Comparative Example C |
|---|---|---|---|
| Thiol (mol/mol of Rh) | Thiophenol 2.0 | tert-butylthiol 2.0 | — |
| Length of run (h) | 108 | 132 | 108 |
| Average rate of formation of phosphine degradation products (mmol/kg × d): | | | |
| $PPh_2Pr$ | 0.24 | 2.73 | 2.49 |
| $PPh_2Bu$ | 0.03 | 0.27 | 0.38 |
| $PPhR_2$ (R = Pr, Bu) | 0.00 | 0.29 | 0.52 |
| S/Rh ratio in | 2.0 | 1.0 | — |

TABLE 2-continued

|  | Example 2 | Comparative Example B | Comparative Example C |
| --- | --- | --- | --- |
| reaction solution at end of run (mol/mol) |  |  |  |

TABLE 3

| Example | Phosphine (mmol) | P/Rh (mol/mol) | Arylthiol (mmol) | Conv. (%) | Aldehyde selectivity (%) | n-content (%) |
| --- | --- | --- | --- | --- | --- | --- |
| Comp. D | Triphenylphosphine (0.6) | 5 |  | 98 | 92 | 97 |
| Comp. E | Triphenylphosphine (1.2) | 10 |  | 99 | 88 | 59 |
| 3 | Triphenylphosphine (1.2) | 10 | Thiophenol (0.24) | 99 | 89 | 68 |
| 4 | Triphenylphosphine (1.2) | 10 | Thiophenol (0.60) | 99 | 87 | 73 |
| 5 | Triphenylphosphine (0.6) | 5 | p-Thiocresol (0.12) | 99 | 87 | 65 |
| 6 | Hexyldiphenylphosphine (1.2) | 10 | Thiophenol (0.12) | 99 | 93 | 72 |

We claim:

1. A process for producing aldehydes by hydroformylating olefinically unsaturated compounds in an organic reaction medium with the aid of a rhodium complex catalyst which is soluble in the reaction medium, which comprises performing the reaction at a pressure of from 1 to 300 bar and at a temperature of from 50° to 160° C. in the presence of a water-insoluble rhodium complex catalyst and also in the presence of an arylthiol of the formula I $$Ar-SH \qquad I$$

where Ar is substituted or unsubstituted aryl.

2. The process of claim 1, wherein Ar is unsubstituted or $C_1$–$C_4$-alkyl- or -alkoxy-monosubstituted, -disubstituted or -trisubstituted phenyl, naphthyl, anthryl or phenanthryl.

3. The process of claim 1, wherein the arylthiol I is used in a molar ratio of from 0.1 to 20 per mole of rhodium.

4. The process of claim 1, wherein the reaction medium contains a rhodium complex catalyst which contains a triorganophosphine or triorganophosphite ligand.

5. The process of claim 1, wherein the reaction medium contains a rhodium complex catalyst which contains triphenylphosphine or hexyldiphenylphosphine as ligand.

* * * * *